United States Patent [19]

Peck et al.

[11] 4,361,580
[45] Nov. 30, 1982

[54] ALUMINUM IBUPROFEN PHARMACEUTICAL SUSPENSIONS

[75] Inventors: Susanne M. Peck; Lois J. Larion; Englebert L. Rowe, all of Kalamazoo, Mich.

[73] Assignee: The Upjohn Manufacturing Company, Arecibo, P.R.

[21] Appl. No.: 259,232

[22] Filed: May 11, 1981

Related U.S. Application Data

[63] Continuation-in-part of Ser. No. 161,599, Jun. 20, 1980, abandoned.

[51] Int. Cl.$^3$ ...................... A61K 47/00; A61K 31/28
[52] U.S. Cl. .................................. 424/287; 424/317; 424/361; 424/362
[58] Field of Search ............... 424/287, 315, 317, 361, 424/362

[56] References Cited

U.S. PATENT DOCUMENTS

| | | | |
|---|---|---|---|
| 3,228,831 | 1/1966 | Nicholson | 424/317 |
| 3,385,886 | 1/1968 | Nicholson | 424/317 X |
| 3,600,437 | 8/1971 | Marshall | 424/317 |
| 3,636,200 | 1/1972 | Zentner | 424/362 X |
| 3,865,857 | 2/1975 | Suzuki | 260/448 R |
| 3,976,674 | 8/1976 | Fields | 424/317 |
| 3,985,779 | 10/1976 | Tanaka | 260/448 R |
| 4,031,243 | 6/1977 | Aparicio | 424/317 |
| 4,145,440 | 3/1979 | Fitch | 424/287 |

FOREIGN PATENT DOCUMENTS 811810  9/1974  Belgium .............................. 424/287

OTHER PUBLICATIONS

Berge, J. Pharm. Sci., vol. 66, Jan. 1977, pp. 1–19.
Nail, J. Pharm. Sci., vol. 65, Aug. 1976, pp. 1195–1198.
Remington's Pharm. Sci., 15th Ed., 1975, pp. 322–327, 1456–1460.
Chem. Abs., vol. 85, 1976, p. 522, Ab. No. 85:192387f.

*Primary Examiner*—Anna P. Fagelson
*Attorney, Agent, or Firm*—John T. Reynolds

[57] ABSTRACT

Aluminum ibuprofen pharmaceutical liquid suspensions having improved resistance to dissolution rate reduction upon storage containing aluminum ibuprofen, a suspending agent have a particle size below 50 microns, a water-soluble surface active agent, water, and preferably also from 5 to 30 grams of sucrose per 100 ml of suspension are disclosed, or its sweetening equivalent of glucose, fructose, sodium saccharin sodium cyclamate, or mixtures thereof.

15 Claims, 2 Drawing Figures

ALUMINUM IBUPROFEN PHARMACEUTICAL SUSPENSIONS

DESCRIPTION

Cross Reference

This is a continuation-in-part of application Ser. No. 161,599, filed June 20, 1980, now abandoned.

INTRODUCTION

This invention relates to pharmaceutical compositions of aluminum salts of ibuprofen. More particularly, this invention provides new gel-resistant, non-caking, liquid pharmaceutical suspensions of aluminum ibuprofen which are easily shakable to a homogeneous consistency for uniform dosing and which have improved resistance to dissolution rate reduction upon storage.

BACKGROUND OF THE INVENTION

Nicholson et al. U.S. Pat. No. 3,385,886 claims 2-(4-isobutylphenyl)propionic acid (ibuprofen) as a compound per se. Nicholson et al. U.S. Pat. No. 3,228,831 discloses the use of ibuprofen as a drug to alleviate the symptoms of inflammation in animals. Since its introduction as a commercially available drug for human use, there has been much medical literature about ibuprofen. Ibuprofen is sold as coated tablets because ibuprofen per se has a bitter, sharply disagreeable taste. The distinct acid taste of ibuprofen is masked by the coating which permits oral administration without giving the bitter or burning acid taste of the free acid. Continued research for better modes in which to administer ibuprofen continues for the purposes of eliminating or reducing the cost of and the need for coatings presently used to overcome as much as possible the disagreeable acid taste of ibuprofen.

It has been found that the usual sodium, calcium and magnesium salts of this acid also contain a discernible disagreeable taste.

Recently, it was discovered that aluminum salts of ibuprofen provide an essentially tasteless, effective pharmaceutical form of ibuprofen which salts can be manufactured economically and compounded into pharmaceutical liquid suspension and solid formulations for administration in unit dosage forms. These aluminum salts are disclosed and claimed in Sinkula U.S. patent application Ser. No. 640,431, filed Dec. 15, 1975, now abandoned but replaced by application Ser. No. 152,238, filed May 22, 1980.

Aluminum ibuprofen salts are not soluble in water or the other pharmaceutical excipients to any substantial extent and they are difficult to wet and disperse uniformly in liquid mixtures. These salts would normally be compounded into any of various solid dosage forms. However, pharmaceutical liquid suspension forms of these salts would be preferred when the patients are to be small children or elderly persons because these patient populations often have difficulty swallowing tablets, capsules or other solid forms of drugs.

In preparing suspensions of water-insoluble drug compounds such as these aluminum ibuprofen salts, the particular pharmaceutical vehicle or diluent mixture which is best for these salts is not readily predictable from knowledge and experience with other similar drug acid salts. Substitution of an aluminum salt of one drug acid into a pharmaceutical formulation of another aluminum salt of a drug acid does not often produce an acceptable pharmaceutical composition for the dosage use intended. See, for example, Belgian Pat. No. 811,810 and the results obtained comparing that formulation in Fitch/Rowe U.S. Pat. No. 4,145,440, Column 9.

To be an acceptable pharmaceutical product the aluminum ibuprofen salt suspension must have a suitable long shelf life, say, one to three years, the liquid suspension must not gel to any significant extent, the solids in the liquid suspension must not settle to form a hard non-uniformly dispersible cake, and the amount of sedimentation of the solids in the suspension must be controlled to within a range of from about 60 to 95 percent of the suspension liquid volume, preferably to about 70 to 85 percent of the suspension liquid volume.

This invention can be considered to be an improvement on the aluminum ibuprofen pharmaceutical suspensions described and claimed in the Fitch/Rowe U.S. Pat. No. 4,145,440. That Fitch/Rowe '440 Patent described pharmaceutical liquid suspension compositions of aluminum ibuprofen salts which are gel-resistant, non-caking, have controlled sedimentation properties and which are easily re-suspended by shaking the suspension bottle by dispersing the aluminum ibuprofen salt in a sorbitol/glycerin/water mixture containing controlled maximum amounts of pharmaceutically acceptable suspending agents and water-soluble surface active agents. Those Fitch/Rowe '440 Patent compositions can also contain small amounts of ethanol, sorbic acid, and sweetening agents such as sucrose, sodium saccharin, and flavoring and coloring agents. Such patent also includes discussion of using an aluminum ibuprofen salt having a ratio of about two ibuprofen equivalents per atom of aluminum in the salt.

Those Fitch/Rowe '440 Patent compositions are effective when used shortly after preparation thereof. However, unexpectedly, it has been discovered that upon long standing on a shelf at various temperature conditions, a problem with those compositions has been observed, the problem being that such Fitch/Rowe '440 compositions, based as they are on a sorbitol/glycerin mixture as part of the liquid vehicle for the suspension, exhibit an aging property of the resulting composition. This aging property has the effect of reducing the dissolution rate of the active ingredient, the aluminum ibuprofen salt, in the liquid suspension to an unacceptably low percentage level when an extended shelf life (say six months or longer) is required for clinical or market acceptance of the suspension as desired product for use world wide for pediatric and geriatric anti-inflammatory therapy applications, which circumstances often require long storage times under varying temperature environments.

Finding this catalytic effect on aging of the composition by the sorbitol/glycerin components in the composition was surprising because there are pharmaceutical literature references such as "Structure of Aluminum Hydroxide Gel III: Mechanisms of Stabilization by Sorbitol" by Steven L. Nail et al. in *Journal of the Pharmaceutical Sciences,* Vo. 65, No. 8, August 1976 pgs. 1195–1198, which indicate that sorbitol, added to aluminum hydroxide gels, was effective in preventing the loss of the acid consuming capacity of the gel (less than ten percent loss) during the six month aging periods, compared to the substantial loss (greater than sixty percent loss) of acid consuming capacity of identical gels which did not contain sorbitol. However, in these aluminum ibuprofen pharmaceutical suspensions it has been found, according to this invention, that sorbitol and glycerin, for some reason not yet fully understood, appear to catalyze the aging and to reduce the dissolution rates of aluminum ibuprofen in these pharmaceutical suspensions. Those in the pharmaceutical chemistry sciences and arts continue to need and search for liquid pharmaceutical suspensions of aluminum ibuprofen salts which are not only gel resistant, non-caking, have controlled sedimentation properties and which suspensions are easily resuspended by shaking the suspension bottle, but also for liquid pharmaceutical suspensions which will not contain ingredients which lower to unacceptable levels the dissolution rate properties of the aluminum ibuprofen contained therein during normal storage periods.

OBJECTS OF THE INVENTION

It is an object of this invention to provide new homogeneously dispersible liquid pharmaceutical suspension compositions of aluminum ibuprofen salts, whose compositions have better dissolution rate properties after periods of storage. It is another object of this invention to improve the aging and dissolution rate properties of aluminum ibuprofen liquid pharmaceutical suspension compositions. Other objects, aspects and advantages of this invention will become apparent from the remaining specification and the claims which follow.

SUMMARY OF THE INVENTION

Briefly, according to this invention, it has been discovered that liquid pharmaceutical suspensions satisfying the above objects can be obtained by suspending the aluminum ibuprofen salt active ingredient in a liquid pharmaceutical suspension containing maximum, controlled amounts of micro-crystalline cellulose, sodium carboxy methylcellulose, or magnesium aluminum silicate suspending agents or mixtures thereof and pharmaceutically acceptable water soluble surface active agents in an aqueous vehicle to obviate or remove the aging problem caused by sorbitol and/or glycerin (of the '440 Patent compositions) and thus increase the dissolution rate over longer periods of storage. It has also been discovered that these improved dissolution rates for the aluminum ibuprofen active ingredient are not materially affected by the addition of or presence of up to about 30 grams of sucrose per 100 ml of liquid suspension composition, or equivalent amounts of sweeteners selected from the group consisting of sucrose, fructose, glucose, sodium saccharin, sodium cyclamate, and mixtures thereof, and thus the addition of these particular sweetening agents can materially aid the taste and acceptability of the suspension to pediatric and geriatric patient populations while still permitting and accomplishing the requirement that the suspension be gel resistant, and non-caking, with controlled sedimentation properties and which settled suspension can easily be re-suspended by shaking the suspension bottle, with only minor affects on the dissolution rate property of the aluminum ibuprofen therein.

DETAILED DESCRIPTION OF THE INVENTION

Figure 1:
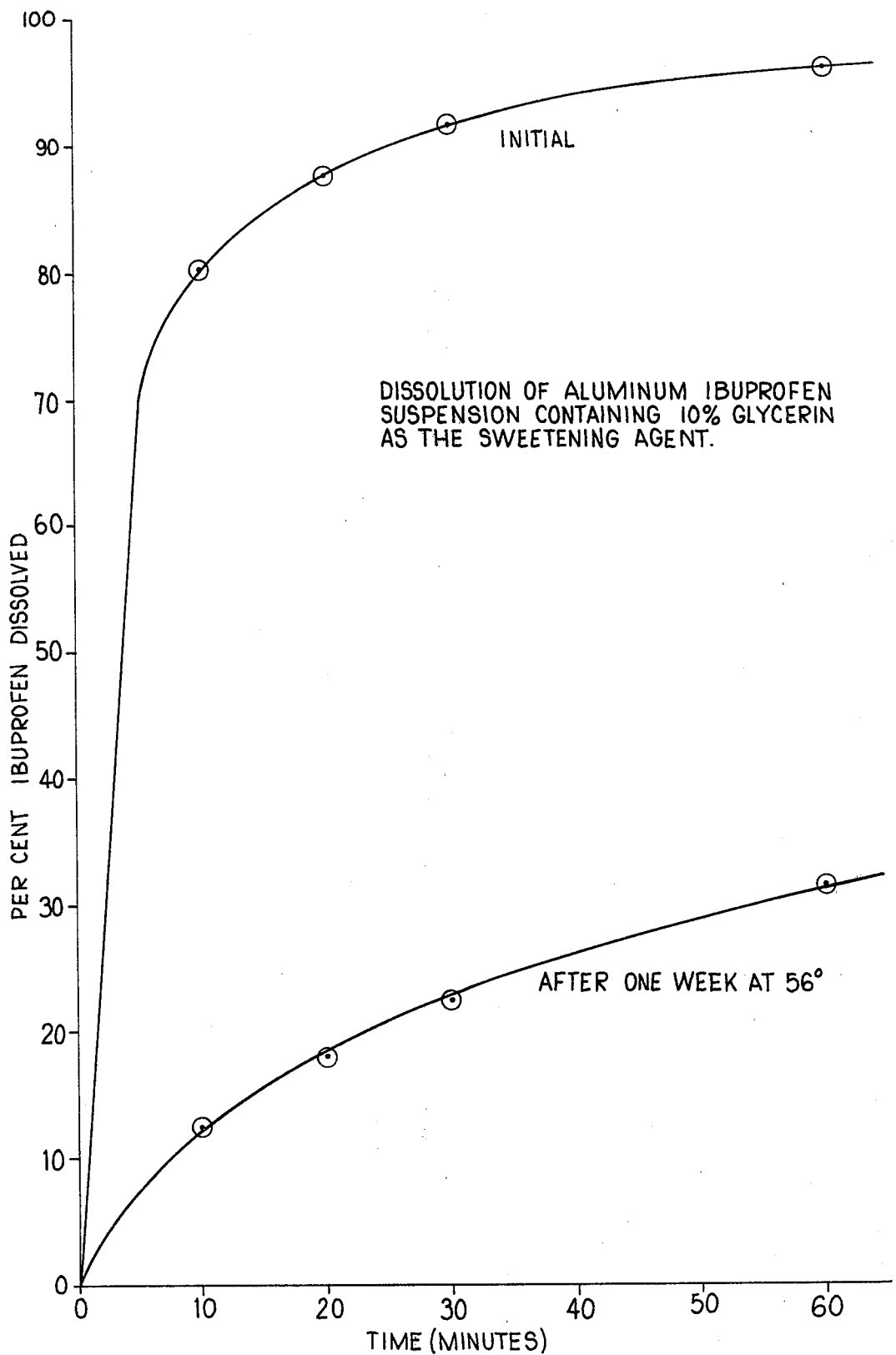

More particularly, this invention provides pharmaceutical liquid suspension compositions comprising, for each 100 ml of suspension, (a) from about 4 to about 17 grams of an aluminum salt of ibuprofen, (b) from about 0.2 to about 1.1 grams of pharmaceutically acceptable suspending agent having an average particle size below about 50 microns, (c) from about 0.3 to about 0.7 grams of a non-toxic, pharmaceutically acceptable essentially water soluble surface active agent, and (d) sufficient water to bring the liquid volume to 100 ml of total liquid suspension.

In addition, the above mixture is treated, if necessary, with sufficient pharmaceutical grade hydrochloric acid or sodium hydroxide or equivalent acid or base aqueous solution to bring the pH of the suspension to between 4.5 and 5.5, preferably to about 5.0. Usually less than 2 ml of ten percent v/v hydrochloric acid solution are required per 100 ml of suspension.

The above compositions contain no sorbitol or glycerin and no sucrose or other saccharide type sugar. Such compositions pass the dissolution rate tests and are acceptable from the point of view of having long term post storage dissolution rate properties for the aluminum ibuprofen salt therein as well as the other above desired properties. However, such compositions have a flat, chalky taste which is not acceptable to most patients.

Preferred compositions of this invention are those described immediately hereinabove which also contain (e) from 5 to 30 grams of granular U.S.P. sucrose in the described 100 ml of liquid suspension composition. It has been discovered surprisingly that these amounts of sucrose do not significantly affect the higher dissolution rate properties of the liquid suspension compositions which do not contain sorbital or glycerin, after extended storage periods.

The preferred suspending agent (b) is selected from the group consisting of:

(1) a mixture of a major amount of microcrystalline cellulose and a minor amount of sodium carboxymethylcellulose (2) a magnesium aluminum silicate powder, and (3) mixtures of (1) and (2), that is, so that the total weight of the suspending agent (1) and (2) mixture is not more than about 1.1 weight percent of the total liquid suspension.

The suspension can also, optionally contain up to about 10 ml of 95 percent ethanol, for each 100 ml of suspension, before the water is added to make the total volume of suspension. The ethanol aids the wetting of the solid ingredients in the suspension.

The composition may also, optionally have added thereto up to about 0.3 mg of sorbic acid, N.F., for each 100 ml of suspension, or other equivalent substance to inhibit the presence, growth and action of mold or yeast.

We have also discovered that in place of part or all of the sucrose, equivalent sweetening amounts of fructose, glucose, sodium saccharin, sodium cyclamate, or mixtures of these sweetening agents can be used without substantially reducing the dissolution rate properties of the aluminum ibuprofen active ingredient therein. Thus, for example, in place of using 5 to 30 grams of sucrose in one of these formulations one can use from about 6.25 grams to about 37.5 grams of glucose, from about 2.94 grams to about 17.65 grams of fructose, from about 5 milligrams to about 60 milligrams of sodium saccharin, from about 166 milligrams to about 1 gram of sodium cyclamate, or equivalent sweetening mixtures of sucrose, glucose, fructose sodium saccharin or sodium cyclamate, as desired.

Examples of flavoring agents which can be included in amounts up to about 1 gram per 100 ml of suspension, include Orange-Lemon Flavor PFC 8432, and other pharmaceutically acceptable flavors, such as Cherry Flavor, Peppermint oil, double distilled eucalyptol, anethol, methyl salicylate, oil cassia or cinnamic aldehyde, and the like.

A preferred composition of all the above generally indicated ingredients according to this invention is one which comprises, for each 100 ml of liquid suspension, (a) about 4.4 to about 14 grams of an aluminum ibuprofen salt, which will provide about 4 to about 12.7 grams of ibuprofen equivalent in the suspension composition;

(b) about 0.2 to 1.1 grams of a suspending agent mixture consisting of about 0.18 to 1.0 grams of microcrystalline cellulose and about 0.02 to about 0.12 grams of sodium carboxymethylcellulose NF low viscosity;

(c) about 0.3 to about 0.7 grams of a surfactant such as (Z)-sorbitan-mono-9-octadecenoate poly(oxy-1,2-ethanediyl)derivatives such as polyoxethylene (20) sorbitan mono-oleate, known in the trade as Polysorbate 80;

(d) from about 5 to about 30 grams of granular U.S.P. sucrose or its sweetening equivalent of glucose, fructose sodium saccharide, sodium cyclamate, or mixtures thereof.

(e) from about 0.1 to about 0.3 grams of sorbic acid NF;

(f) from about 0.032 to 0.05 ml of artificial Cherry-Vanilla Flavor;

(g) 10 percent v/v hydrochloric acid aq. solution q.s. (for pH adjustment);

(h) 10 percent w/v sodium hydroxide aq. solution q.s. (for pH adjustment)

(i) Purified water q.s. ad to 100 ml.

In a typical preferred aluminum ibuprofen liquid suspension of the above type, that is, an example of a specific liquid suspension composition we use, for each 100 ml of liquid suspension composition, (a) about 8.8 grams of an aluminum monohydroxy bis(2-(4-isobutylphenyl)propionate salt, referred to herein as a 1:2 aluminum:ibuprofen salt, preferably such a salt, referred to herein as a 1:2 aluminum:ibuprofen salt, preferably such a salt powder having at least 7 square meters of surface area per gram, (8.8 grams of pure anhydrous aluminum ibuprofen, 1:2, will provide 8.0 grams of ibuprofen equivalent when hydrolyzed);

(b) about 0.5 grams of a suspending agent comprising about 89 percent, by weight, microcrystalline cellulose and 11 percent, by weight, of sodium carboxymethylcellulose NF low viscosity, (AVICEL® RC-591);

(c) about 0.5 grams of Polysorbate 80 USP;

(d) about 15 grams of sucrose USP;

(e) about 0.2 grams of sorbic acid NF, (f) about 0.05 ml of artificial Cherry Vanilla Flavor;

(g) sufficient 10 percent v/v hydrochloric acid aq. solution to bring pH to 5.0, and (h) Purified water, q.s to 100 ml.

To prepare a liquid suspension composition of the above type, we follow the following procedure:

Add the microcrystalline cellulose and sodium carboxymethylcellulose suspending agent to one-half of the purified water (for the lot size desired) in a tared, calibrated, stainless steel, or equivalent tank. Mix well for thirty minutes. Add the sorbic acid and Polysorbate 80 and mix until dispersed.

Add the sucrose or other sweetening agent and flavor and mix until dispersed.

Add the aluminum ibuprofen salt slowly with rapid mixing while avoiding excess air entrapment. Stir until the mixture is completely wetted, then reduce the mixing speed to a slow roll to release air, until the mixture is a fluid with no foam.

The batch can optionally be allowed to stand overnight at this point, and then stirred again to ensure air removal. When air is sufficiently released, adjust pH to about 5 with the hydrochloric acid and q.s. the mixture with the remaining purified water to the total volume desired. The mixture is passed through a colloid mill to break up aggregates and then stirred slowly to release entrapped air.

The aluminum ibuprofen salt in the suspension is a salt of the formula I where x is 0 to 2, y is 1 to 3, so that the sum of x and y is equal to 3. This formula is intended to include mixtures of mono-ibuprofen aluminum salt, di-ibuprofen aluminum salt and tri-ibuprofen-aluminum salt molecules so that in a typical aluminum salt sample the average ratio of ibuprofen moiety to aluminum atom in the sample can range between, say 0.9 and 2.9. The preferred aluminum ibuprofen salts for use in these compositions are those having an average ratio of between about 1 and 2 ibuprofen acid equivalents per aluminum atom ($x=1$ to 2; $y=1$ to 2). We are developing an aluminum ibuprofen suspension of this invention using an aluminum ibuprofen salt which contains an average of about two ibuprofen moieties per atom of aluminum, although aluminum ibuprofen salts containing down to about 1 equivalent of ibuprofen per aluminum atom work very well in these suspensions. Aluminum ibuprofen salts containing close to the maximum ratio of three ibuprofen equivalents per aluminum atom can be used but they are not preferred because they are difficult to purify from adhering ibuprofen, which, as indicated above, contributes to a disagreeable taste and because in aqueous media they hydrolyze partially to hydroxy aluminum ibuprofen salts and free ibuprofen.

The preferred aluminum monohydroxy bis-ibuprofen salt for use in these suspensions can be prepared by the general method of Sinkula, supra, 2[ibuprofen Na+]+AlCl$_3$+NaOH (ibuprofen)$_2$-AlOH+3NaCl where "ibuprofen" denotes the anionic form of 2-(4-isobutylphenyl)propionic acid. Dihydroxy mono-ibuprofen aluminum salt ($x=2$ and $y=1$) also produces good liquid suspensions in these formulations. A typical run, on a small scale of that procedure, can be described as follows:

Aluminum Ibuprofen 1:2 Salt

A stirred solution of sodium ibuprofen (22.8 g, 0.1 mole) in 200 ml of dionized water is heated to 65° C. and treated at the rate of 10 ml/min with a solution of aluminum chloride hexahydrate (10.84 g, 0.0449 mole) in 100 ml deionized water. The pH was monitored and held constant at 7.1–7.3 throughout most of the reaction by the addition of 43 ml of 1.0 N NaOH (0.043 mole). The temperature is allowed to drop to 50° C. and a white solid is collected by filtration. The solids are washed with water (6 × 100 ml) and the wet cake air dried. Final drying is done at room temperature for three hours over phosphorous pentoxide using high vacuum.

Analysis Calc'd for $C_{26}H_{35}O_5Al$: C, 68.70; H, 7.76; Al, 5.93; Found (corrected for water): C, 68.87; H, 7.69; Al (Ash), 6.24; Al (EDTA) 6.31; H$_2$O 0.77.

Optionally, the aluminum monohydroxy bis-ibuprofen salt obtained before drying can be washed with hydrochloric acid aqueous solutions, say, with sufficient 0.01 to 0.1 N hydrochloric acid to adjust the pH of the aluminum bis-ibuprofen salt/aqueous acid solution mixture to about 3 to 3.5 for about one hour to further purify the salt.

Aluminum monohydroxy bis-ibuprofen salts prepared in this manner have significantly higher surface area properties than aluminum ibuprofen salts prepared by prior art suggested methods such as the aluminum triethyl or aluminum isobutoxide diethyl methods set forth in Suzuki et al. U.S. Pat. No. 3,865,857 and German Offenlegungsschrift No. 2,213,704. Aluminum mono-hydroxy bis-ibuprofen salts can be prepared by this above herein-described Sinkula method having surface areas in excess of 7 square meters per gram, making the aluminum ibuprofen salts capable of delivering fully bioequivalent dosages in reasonably small drug vehicle amounts of ibuprofen equivalent as are obtained by present ibuprofen acid drug forms.

These new suspensions are designed and prepared so as to contain per a 5 ml dose between about 200 mg and about 600 mg of ibuprofen equivalent in the form of the aluminim ibuprofen salt. The weight percent of the aluminum ibuprofen salt is used which corresponds to the selected concentration. For example, for a pediatric suspension containing, say, about 200 mg of ibuprofen equivalent per 5 ml dose, the weight of an aluminum di-ibuprofen salt per 100 ml of suspension being prepared would be about 4.4 grams. For a normal adult size 400 mg dose of ibuprofen equivalent the weight content of the same aluminum di-ibuprofen salt would be about 8.8 grams and for a stronger 600 mg dose of ibuprofen equivalent, the dosage of such di-ibuprofen aluminum salt would be about 13.2 grams of this aluminum di-ibuprofen salt per 100 ml of suspension.

Because these are pharmaceutical suspensions, the grade of sucrose must be acceptable for pharmaceutical purposes, but tests at varying sucrose concentrations from 5 to 30 percent, w/v, indicate that variations in the dissolution rate of aluminum ibuprofen ($A_{60}$) appears to be random and not correlatable to the sucrose content in the liquid suspension. The range of sucrose content in these liquid suspension compositions can be dictated by taste considerations. At least about 5 percent, w/v, of sucrose is needed for minimal sweetness and taste masking, if sucrose is to be the only sweetening agent in the composition, while sucrose contents above 25 percent, w/v, cause the suspensions to be too sweet. Viscosity and sedimentation properties of these liquid suspensions are not significantly affected over the 5 to 25 percent sucrose content range. At the preferred sucrose mid-range concentration (about 15 percent w/v) these liquid suspension formulations will provide about 0.75 gram of sucrose per 5 ml dose of the liquid suspensions.

Further, as the particle size of aluminum ibuprofen salt component in these liquid suspensions becomes finer and finer, say, sizes small enough to have surface areas approaching and preferably exceeding 7 square meters per gram, preferably, at this time, in the range of 12 to 16 square meters per gram, the viscosity of the suspension for an indicated amount of suspending agent in the suspension will tend to increase. This viscosity increase can be offset, if desired, by lowering the content of the suspending agent. For example, with our preferred finely divided aluminum bis-ibuprofen salt suspension compositions, the weight percent of the microcrystalline cellulose and sodium carboxymethylcellulose suspending agents amounts can be reduced to as much as one-half the amounts expressed in the Fitch/Rowe '440 Patent.

The suspending agents useful in the suspensions of this invention include Acacia U.S.P., Bentonite U.S.P., Carbomer N.F., Carboxymethylcellulose sodium U.S.P., Polyvinyl alcohol U.S.P., Povidone U.S.P., Tragacanth U.S.P., Xanthan Gum NF, Microcrystalline Cellulose N.F., and the like, which for the most part are powders having average particle sizes below about 50 microns.

Examples of preferred suspending agents for use in the pharmaceutical suspensions of this invention include:

(1) Avicel ® RC-591, which is a commercially available microcrystalline cellulose marketed by FMC Corporation, Avicel Department, Marcus Hook, Pa., 19601, and which is said to be a colloidal form of about 89 percent miro-crystalline cellulose gel blended with about 11 percent sodium carboxymethyl-cellulose and dried, and which product is easily dispersed in water. It is insoluble in water, organic solvents and dilute acids. It is partially soluble in dilute alkali. Its physical and chemical specifications according to the national Formulary, Vol. XIV, are: Loss on Drying: not more than 8% of its weight; Heavy metals: less than 0.001% or 10 parts per million; viscosity of a 1.2 percent dispersion: $65 \pm 25$ centipoise; pH of a 1.2 percent dispersion; 6 to 8; and assay:sodium carboxymethylcellulose content 11 (8.25 to 13.75) percent. Other similar pharmaceutical grade microcrystalline cellulose products can be used.

(2) Veegum ® F is a microfine powdered magnesium aluminum silicate manufactured and sold by R. T. Vanderbilt Company, Inc., Specialties Department, 230 Park Avenue, New York, N.Y. 10017. This powdered suspending agent is said to be an inorganic, complex, colloidal magnesium aluminum silicate having an average chemical analyses, expressed as oxides as follows:

| | |
|---|---|
| Silicon dioxide | 61.1 Percent |
| Magnesium oxide | 13.7 Percent |
| Aluminum oxide | 9.3 Percent |
| Titanium oxide | 0.1 Percent |
| Ferric oxide | 0.9 Percent |
| Calcium oxide | 2.7 Percent |
| Sodium oxide | 2.9 Percent |
| Potassium oxide | 0.3 Percent |
| Carbon dioxide | 1.8 Percent |
| Water of combination | 7.2 Percent | which has a particle size which passes a 326 mesh screen.

We have found that for pharmaceutical liquid suspensions of aluminum ibuprofen meeting the above criteria, it is important to control the amount of suspending agent ranging from at least about 0.2 weight percent to about 1.1 percent by weight, preferably below about 2 percent, the particular amounts depending upon the choice of suspending agent. If the weight amounts of suspending agents are below the lower limits stated, the material does not suspend properly and, as a result, the solid components of the suspension precipitate to form a cake which is difficult to disperse; if the amounts of the suspending agents are much above the (1.1) weight percent range, the suspension becomes excessively thick and does not flow.

The wetting agents or surface active agents used in the suspension of this invention must be pharmaceutically acceptable, that is, non-toxic, and essentially water soluble in the amounts used and be effective to keep the solid form ingredients soluble or compatible with the suspension formulation. The wetting agent or surface active agent can be a non-ionic, anionic or cationic chemical compound or composition which should perform its function at a concentration of no more than about 0.8 weight percent, based on about 100 ml of liquid suspension. Examples of preferred water soluble wetting agents or surfactants for these aluminum ibuprofen suspensions include Polysorbate 80 (polyoxyethylene(20)sorbitan monooleate), Polysorbate 60 (polyoxyethylene(20)sorbitan monostearate), Myrj 52 (polyoxyethylenestearate U.S.P.), glycerol monostearate, glycerol monooleate, glycerol monoricinoleate, Pluronic F-68 (a polyoxyethylenepolyoxypropylene copolymer containing about 80 percent polyoxyethylene units and a polyoxypropylene moiety whose molecular weight is about 1750) as non-ionic surfactants, sodium lauryl sulfate as an anionic surfactant, and myristyl gamma-picolinium chloride as a cationic surfactant.

This invention is further illustrated, compared and exemplified by the following detailed preparations and examples, but they are not intended as limiting the scope of the invention.

PREPARATION I

Illustrative of Fitch/Rowe U.S. Pat. No. 4,145,440

Sorbitol/Glycerin Vehicle

| Ingredients | Quantity |
|---|---|
| Avicel RC-591 ® (a blend of 89% microcrystalline cellulose and 11% sodium carboxymethylcellulose NF low viscosity) | 1.0% |
| Carboxymethylcellulose Sodium USP Low viscosity | 0.2% |
| Glycerin USP | 10.0% |
| Sorbic Acid NF | 0.2% |
| Polysorbate 80 USP Food Grade | 0.5% |
| Sorbitol Solution 70% USP | 20.0% |
| Aluminum Ibuprofen 1:2 salt | 8.8% |
| 30% Solution Sodium Hydroxide | (to adjust pH) |
| Purified water USP q.s. ad | 100.0% |

Directions

Disperse Avicel in ~50% of the purified water while stirring at high speed for one-half hour. Wet the carboxymethylcellulose sodium with ~one-third of the glycerin and add to the Avicel dispersion. While stirring constantly at a moderate speed, add the remainder of the glycerin, sorbic acid, polysorbate 80 and sorbitol solution. Mix well. Add the aluminum ibuprofen while stirring rapidly. Adjust to final volume with purified water. Adjust pH to 5.0, homogenize, and stir slowly to remove excess air.

Observations

Effect of Storage Conditions on Dissolution

| Age | Temp. | $A_{60}$* |
|---|---|---|
| Initial | — | 100.1/100.5 |
| 1 week | 47° | 72.0/67.2 |
| 1 week | 56° | 38.1/38.1 |
| 1 week | 70° | 33.8/33.7 |
| 1 week | 90° | 22.4/23.3 |
| 4 mos. | RT | 67.8/70.8 |

*$A_{60}$ is the percent dissolved in one hour in pH 7.2 buffer at 37° C. A full description of the dissolution system is given below.

Appearance 9 months ambient storage—slight sedimentation, resuspends easily.

This formulation has excellent properties: non-caking, resistance to gelling, good sedimentation, chemical stability and elegance. However, upon aging, the dissolution rate decreases drastically as indicated above. The present invention, as shown by the following examples, is a significant improvement over Example I.

Example I

Sucrose vehicle

| Ingredients | Quantity |
|---|---|
| Avicel RC-591 ® (a blend of 89% microcrystalline cellulose and 11% sodium carboxymethylcellulose) | 1.0% |
| Sorbic Acid NF | 0.2% |
| Polysorbate 80 USP Food Grade | 0.5% |
| Sucrose USP Granular | 15.0% |
| Aluminum Ibuprofen 1:2 Salt (5% excess) | 9.63% |
| Cherry-Vanilla flavor | 0.032% |
| Purified Water USP q.s. ad | 100.0% |

Directions

Add the Avicel to ~50% of purified water. Mix well for about thirty minutes while heating to 50° C. Add the polysorbate 80 and sorbic acid and mix until dispersed. Add the sucrose and flavoring and mix until dispersed. Add the aluminum ibuprofen and stir slowly until completely wetted. Pass suspension through a colloid mill, adjust pH to 5.0 and q.s. to final volume with purified water.

Observations

Effect of Storage Conditions on Dissolution

| Age | Temp. | $A_{60}$ |
|---|---|---|
| 1 week | 25° | 10.54/107.6 |
| 1 week | 56° | 93.3/92.9 |
| 1 month | 47° | 97.8/100.6 |

Appearance 4 months—slight sedimentation and gelling, suspension readily resuspends upon shaking.

This formula exhibits excellent sedimentation properties, elegance, etc. just as Preparation I does. However, it is superior to Preparation I in that the dissolution rate does not change significantly upon aging. The substitution of sucrose for sorbitol and glycerin has made the difference and it appears as if sorbitol and/or glycerin are responsible for the poor aging.

A series of experimental batches were made in order to determine the important factors in this aging phenomenon. The following four examples show that sorbitol and glycerin are the cause of decreasing dissolution rate.

PREPARATION II

Formula: No sorbitol

| Ingredients | Quantity |
| --- | --- |
| Avicel RC-591 ® (a blend of 89% microcrystalline cellulose and 11% sodium carboxymethylcellulose NF low viscosity) | 1.0% |
| Carboxymethylcellulose sodium USP Low Viscosity | 0.2% |
| Glycerin USP | 10.0% |
| Polysorbate 80 USP Food Grade | 0.5% |
| Sorbic Acid NF | 0.1% |
| Aluminum Ibuprofen 1:2 salt | 8.8% |
| 10% Solution Hydrochloric Acid | (to adjust pH) |
| Purified Water USP q.s. ad | 100.0% |

Directions

Disperse Avicel in ~50% of the purified water while stirring at high speed for ~one-half hour. Wet the carboxymethylcellulose sodium with ~one-third of the glycerin and add to the Avicel dispersion. While stirring constantly at a moderate speed, add the remainder of the glycerin, sorbic acid, and polysorbate 80. Mix well. Add the aluminum ibuprofen while stirring rapidly. Q.S. to final volume with purified water, adjust pH to 5.0, and homogenize.

Observations

Effect of Storage Conditions on Dissolution

| Age | Temp. | $A_{60}$ |
| --- | --- | --- |
| Initial | — | 94.3 |
| 1 week | 56° | 24.5 |

Appearance 8 months—thick, smooth suspension, resuspends upon shaking.

PREPARATION III

Formula: No glycerin

| Ingredients | Quantity |
| --- | --- |
| Avicel RC-591 ® (a blend of 89% microcrystalline cellulose and 11% sodium carboxymethylcellulose NF low viscosity) | 1.0% |
| Carboxymethylcellulose Sodium USP Low Viscosity | 0.2% |
| Sorbic Acid NF | 0.1% |
| Polysorbate 80 USP Food Grade | 0.5% |
| Sorbitol Solution 70% USP | 20.0% |
| Aluminum Ibuprofen 1:2 salt | 8.8% |
| 10% Solution Hydrochloric Acid | (to adjust pH) |
| Purified Water USP q.s. ad | 100.0% |

Directions

Disperse Avicel in ~50% of the purified water while stirring at a high speed for ~one-half hour. Add the carboxymethylcellulose sodium, sorbic acid, polysorbate 80 and sorbitol solution and mix well. Add the aluminum ibuprofen while stirring rapidly. Q.S. to final volume with purified water, adjust pH to 5.0 and homogenize.

Observations

Effect of Storage Conditions on Dissolution

| Age | Temp. | $A_{60}$ |
| --- | --- | --- |
| Initial | — | 102.8 |
| 1 week | 56° | 34.3 |

Appearance 8 months—thick, smooth suspension, resuspends upon shaking.

EXAMPLE II

Formula: No sorbitol solution or glycerin

| Ingredients | Quantity |
| --- | --- |
| Avicel RC-591 ® (a blend of 89% microcrystalline cellulose and 11% sodium carboxymethylcellulose NF low viscosity) | 1.0% |
| Carboxymethylcellulose Sodium USP Low viscosity | 0.2% |
| Sorbic Acid NF | 0.1% |
| Polysorbate 80 USP Food Grade | 0.5% |
| Aluminum Ibuprofen 1:2 salt | 8.8% |
| 10% Solution Hydrochloric Acid | (to adjust pH) |
| Purified water USP q.s. ad | 100.0% |

Directions

Disperse Avicel in ~50% of the purified water stirring at a high speed for ~one-half hour. Add the carboxymethylcellulose sodium, sorbic acid and polysorbate 80 and mix well. Add the aluminum ibuprofen while stirring rapidly. Q.S. to final volume with purified water, adjust pH to 5.0, and homogenize.

Observations

Effect of Storage Conditions on Dissolution

| Age | Temp. | $A_{60}$ |
| --- | --- | --- |
| Initial | — | 96.4/101.0 |
| 1 week | 56° | 100.2/97.5 |

Appearance 8 months—sedimented slightly, resuspends easily.

EXAMPLE III

| Ingredients | Quantity |
| --- | --- |
| Aluminum Ibuprofen 1:2 salt | 8.8% |
| Polysorbate 80 USP Food Grade | 0.5% |
| Purified Water USP q.s. ad | 100.0% |

Directions

Add the Polysorbate 80 to ~50% of the purified water and mix well. Add the aluminum ibuprofen while stirring rapidly. Stir for ~three days, q.s. to volume with purified water and homogenize at tight setting.

Observations

Effect of Storage Conditions on Dissolution

| Suspension | Age | Temp. | $A_{60}$ |
|---|---|---|---|
| A | 1 week | RT* | 93.8 |
| B | 1 week | 56° | 93.1 |

RT* = Room Temperature

Appearance

Suspension readily sediments and has a tendency to cake.

The above preparations and examples clearly show that both sorbitol and glycerin cause aluminum ibuprofen to become less reactive, i.e., hydrolyze and dissolve more slowly. This was unexpected since prior experimental work on an analogous compound showed that sorbitol and other polyhydroxy compounds actually inhibited the decreasing reactivity of $Al(OH)_3$ that normally occurs on aging. See S. L. Neil et al., *J. Pharmaceutical Sciences*, 65, 1195 (1976). The effect can be explained by hydrogen bonding between the hydroxyl groups of sorbitol and the edge of the hydroxy aluminum particles which inhibits the secondary polymerization reaction. It was surprising, then, that sorbitol would actually catalyze the aging effect of these aluminum salts. In addition, it was totally unexpected that sucrose would behave so differently from other sweetening agents.

Dissolution Test Method

A dissolution test method for the purpose of obtaining comparable dissolution rate numbers for various aluminum ibuprofen liquid suspensions is given below:

| Dissolution Conditions | |
|---|---|
| Apparatus: | RFSB dissolution system* |
| Sample size: | 2.0 ml aluminum ibuprofen suspension (80 mg/ml) |
| Dissolution Fluid: | 900 ml 0.05M $KH_2PO_4$ pH 7.2 buffer |
| Temperature: | 37° C. |
| Agitation Speed: | 600 rpm |
| Filter: | ½ μm glass filter |

*Rotating filter - stationary basket system. U.S. Pat. No. 3,801,280, ACShah and CBPeot (to The Upjohn Co.), April 2, 1974

Procedure for Dissolution Studies

The equivalent weight of 2.0 ml of suspension (based on the specific gravity of the suspension) is added at time zero to each beaker containing 900 ml of pH 7.2 buffer. The containers are rinsed and the washing added to the dissolution beakers. 10.0 ml of filtrate are withdrawn manually at specified times and placed in 20 ml scintillation vials. Intermittent pumping is used prior to sampling to obtain a uniform sample of filtrate. An empty basket is inserted to eliminate any vortex. All samples are immediately refiltered through a 0.45 μm millipore filter. 1 N NaOH solution is added to each beaker after sampling to adjust pH of phosphate buffer to ca 11.0. A final sample is withdrawn after twenty-four hours in order to assay for total amount of ibuprofen present. This concentration is used as $D_{100}\%$, the theoretical amount ibuprofen present.

High Pressure Liquid Chromatography Conditions

| | |
|---|---|
| Column: | EM Hibar II Lichrosorb RP-8, 10 μm, or equivalent Reverse phase column |
| Solvent: | Acetonitrile-pH 7.2 phosphate buffer 40:60; pH adjusted to 7.3. |
| Internal Standard: | 0.002M acetophenone in pH 7.2 phosphate buffer |
| Flow Rate: | 1.5 ml/min |
| Pressure: | 1000–1500 psi |
| Pump: | Altex 110A Solvent Metering Pump, or equivalent |
| Detector: | Hitachi 100-40 UV-VIS variable wavelength spectrophotometer, or equivalent |
| Wavelength: | 230 nm |
| Slit Width: | 2.0 nm |
| Scale Setting: | 0.3 ABS |
| Attenuation: | 128 |
| Integrator: | HP 3380A integrator-recorder, or equivalent |
| Sampler: | WISP 710 automatic sampler, or equivalent |
| Sample size injected: | 50 μl |

Alternate High Pressure Liquid Chromatography Assay Conditions

| | |
|---|---|
| Column: | Microbondapak $C_{18}$ reversed phase (Waters) or equivalent |
| Pump: | Dual head LDC (Milton Roy Minipump), or equivalent |
| Detector: | UV using a Beckman DUR Spectrophotometer, or equivalent |
| Injector: | Rheodyne loop (20 μl) injector, or equivalent |
| Scale setting: | 0–0.56 AUFS |
| Solvent: | UV acetonitrile-water-acetic acid (50:50:0.5) |
| Sample: | 20 μl containing 0.05–0.5 mg/ml |
| Flow rate: | 2.5 ml/min |
| Wavelength: | 228 nm |

External Standard Preparation

External standard is prepared by dissolving a known amount of ibuprofen in 7.2 phosphate buffer. Repetitive injections are made and an average amount/area ratio of internal standard and ibuprofen standard is used in programming the integrator.

Sample Preparation

Equal volumes of sample filtrate and internal standard solution are mixed and then an aliquot of this mixture is injected on the column.

Calculation of Percent Ibuprofen Dissolved

The Internal standard method using the HP 3380 integrator is used in calculating concentration of ibuprofen in samples.

Example: Theoretical amount ($D_{100}\%$) of ibuprofen present in 2.0 ml of suspension = 160 mg.

$$\frac{160 \text{ mg ibuprofen}}{902 \text{ ml dissolution fluid}} = 0.1774 \text{ mg ibuprofen/ml}$$

EXAMPLE IV

Comparison of effect on aluminum ibuprofen dissolution rates ($A_{10}$) by various saccharides and sweeting agents.

A number of sweetening agents which are commonly used in liquid pharmaceutical formulations for oral use were incorporated into a standard formulation, set forth below, and then tested by means of a dissolution rate test.

The test formulation was as follows:

| Ingredients | Quantity per 100 ml |
| --- | --- |
| Microcrystalline cellulose and carboxymethylcellulose sodium N.F., low viscosity | 0.5 gm |
| Polysorbate ®80 N.F. | 0.5 gm |
| Sorbic Acid N.F. | 0.2 gm |
| Cherry vanilla flavor | 0.005 ml |
| Aluminum ibuprofen, as in Preparation 1, above | 8.8 gm |
| 10% solution hydrochloric acid to adjust pH to 5.0 | — |
| Test sweetening Agent (Sucrose) | 10 gm |
| Purified water, q.s., ad | 100 ml |

In these tests, 10 grams of each sweetener was used, regardless of its relative sweetness, to determine the respective affects of the test sweetener on the dissolution rate of the aluminum ibuprofen active ingredient in the respective formulations. It is understood that when the desired sweetener is selected, the weight amount thereof will be adjusted within the above indicated ranges in the total formulation to obtain as closely as possible a desired degree of sweetness in the formulations.

The respective test liquid pharmaceutical suspensions were tested within a few days after preparation (initial $A_{10}$ values) and then tested again after storage of a portion of the same pharmaceutical liquid suspension for one week at 56° C. (one week 56° C. $A_{10}$ value). This accelerated aging simulates (in the laboratory) longer term aging at 25° C. in warehouse storage.

The dissolution rate test is run as follows:

Two ml of the test suspension are added at time zero to 900 ml of pH 7.2 phosphate at 37° C. The liquid mixture is stirred continuously at 600 rpm. by means of a rotating filter apparatus. Samples of the stirred mixture are taken periodically, filtered and assayed for dissolved ibuprofen (free acid) content by high pressure liquid chromatography. Examples of typical dissolution curves for glycerin and sucrose test sweeteners are attached hereto as FIGS. 1 and 2, respectively.

The percent ibuprofen (free acid) dissolved in 10 minutes ($A_{10}$) is an effective dissolution parameter for comparing the effect of the test sweetener (or blank) on the dissolution rate of the aluminum ibuprofen in the respective test suspension.

The suspensions dissolve more slowly as they age, even the very simplest suspensions containing only aluminum ibuprofen and the surfactant. The following commonly used pharmaceutical excipients (for sweetening) cause a substantially more serious aging effect as measured by the $A_{10}$ value after one week of storage in the accelerated aging test at 56° C.

| Test Sweetening Agent | $A_{10}$, % | |
| --- | --- | --- |
| | Initial | After 1 week/56° C. |
| Glycerin | 80.5 | 12.6 |
| Sorbitol/Glycerin (50/50 w/v) | 93.7 | 9.2 |
| Xylitol | 86.8 | 23.9 |
| Manniol | 90.9 | 48.0 |

| Test Sweetening Agent | $A_{10}$, % | |
| --- | --- | --- |
| | Initial | After 1 week/56° C. |
| Arabitol | 89.8 | 46.6 |

The following group of compounds are uniquely different from the above sweetening agents in that they are pharmaceutically acceptable sweeteners which do not cause substantial reduction of the dissolution rate with the test period of time.

| Test Sweetening Agent | $A_{10}$, % | |
| --- | --- | --- |
| | Initial | After 1 week/56° C. |
| None | 85.1 | 69.2 |
| Sucrose | 92.8 | 59.8 |
| Fructose | 89.5 | 60.4 |
| Glucose | 90.7 | 59.3 |
| Sodium Saccharin | 90.0 | 63.4 |

In the drawings, FIG. 1 shows graphically the relationship between the percent ibuprofen dissolved (ordinate) over time periods of up to 1 hour (abcissa) from alumina ibuprofen pharmaceutical suspensions prepared as above combining 10 percent w/v of glycerin as the sweetening agent initially (top line) and after one week of 56° C. aging of the suspension. The FIG. 1 graph shows that the $A_{10}$ value for the initial sample is about 80.5% dissolved and the $A_{10}$ value for the one week accelerated aged sample is about 12.5% dissolved.

Figure 2:
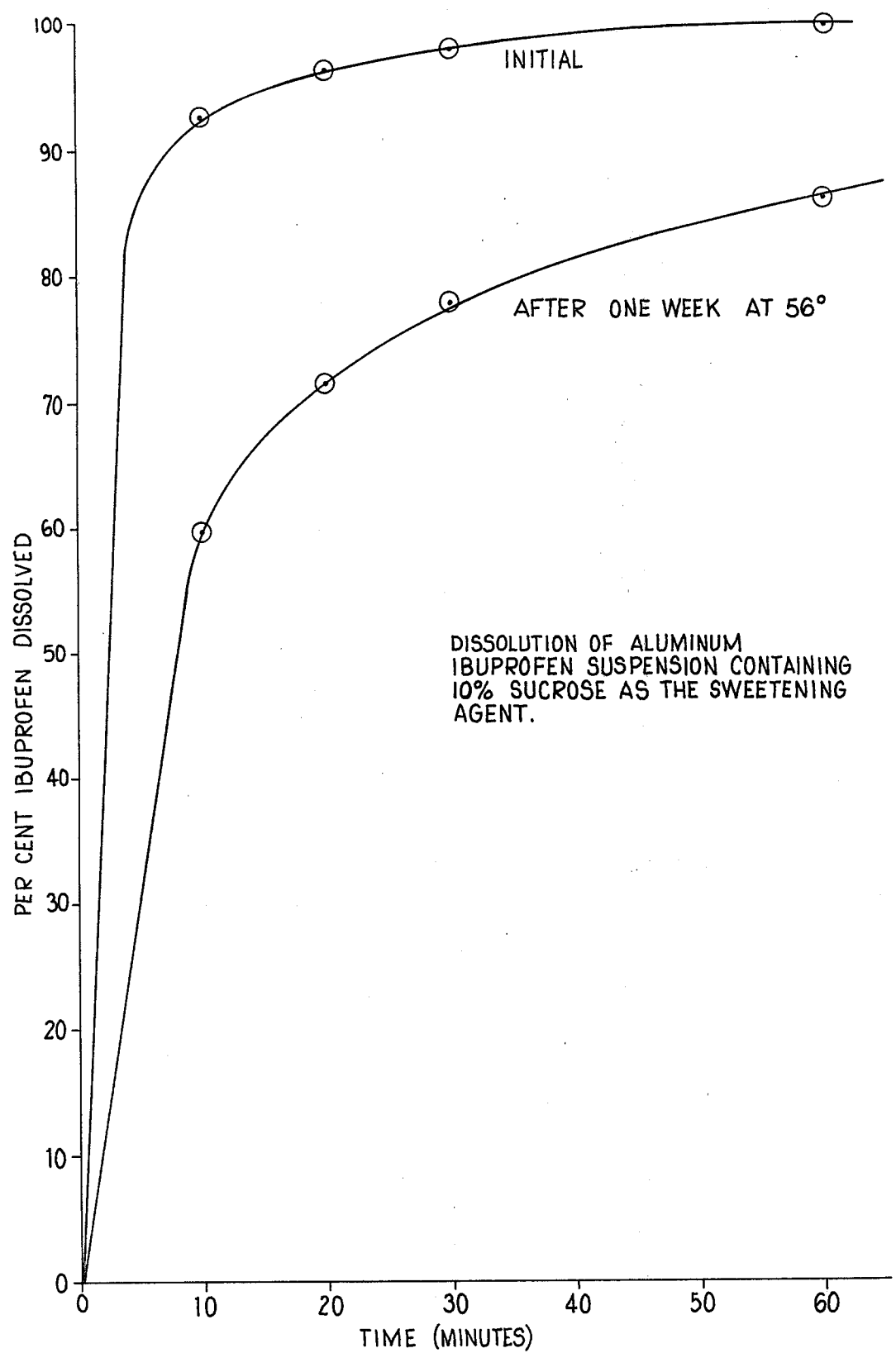

In FIG. 2, in a similar graph of the relationship between the percent ibuprofen dissolved initially, and after 1 week of 56° C. aging of aluminum ibuprofen pharmaceutical suspensions using vertical suspensions using 10 percent w/v of sucrose as the sweetening agent, the graph shows that the reduction of ibuprofen dissolution rate is not nearly as great using sucrose as the sweetener. The FIG. 2 graph shows that the initial $A_{10}$ value for the sucrose containing pharmaceutical formulation is about 92.5 percent and that the one week 56° C. aging $A_{10}$ value of the same sucrose formulation is about 60 percent.

FORMULAS

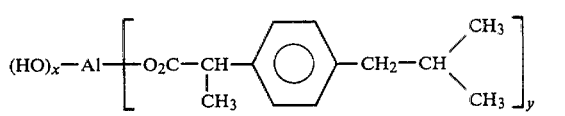

$$(HO)_x-Al\left[-O_2C-CH(CH_3)-\underset{}{\bigcirc}-CH_2-CH\begin{matrix}CH_3\\CH_3\end{matrix}\right]_y \quad I$$

We claim:

1. A pharmaceutical liquid suspension composition consisting essentially of, for each 100 ml of suspension,
   (a) from about 4 to about 17 gms of an aluminum salt of ibuprofen,
   (b) from about 0.2 to about 1.1 gms of a pharmaceutically acceptable suspending agent having an average particle size below about 50 microns,
   (c) from about 0.3 to about 0.7 gms of a non-toxic pharmaceutically acceptable essentially water soluble surface active agent, and
   (d) sufficient water to bring the liquid volume to 100 ml of total liquid suspension.

2. A composition according to claim 1 which further includes (e) from 5 to about 30 gms of sucrose, or its sweetening equivalent of a compound selected from the group consisting of fructose, glucose, sodium saccharin, sodium cyclamate or mixtures thereof.

3. A composition according to claims 1 or 2 wherein the suspending agent is selected from a group consisting of
   (1) a mixture of about 0.18 to about 1.0 weight percent of microcrystalline cellulose and about 0.02 to about weight percent of sodium carboxymethylcellulose,
   (2) and about 0.12 to about 1.0 weight percent of magnesium aluminum silicate powder, and
   (3) mixtures of (1) and (2), so that the total weight of the suspending agent (1) and (2) to mixture is not more than about 1.1 percent.

4. A composition according to claims 1 or 2 which further includes up to about 10 ml of 95% ethanol for each 100 ml of suspension before the last of the q.s. water is added.

5. A composition according to claims 1 or 2 which further includes up to about 0.3 mg of sorbic acid for each 100 ml of suspension before the last of the q.s. water is added.

6. A composition according to claim 2 which includes as component (e) from 5 to about 30 grams of sucrose.

7. A composition according to claims 1 or 2 which further contains one or more flavoring and coloring agents as required, before the last of the q.s. water is added.

8. A composition according to claims 1 or 2 wherein the aluminum ibuprofen salt is one having an average ratio of between about 1 and 2 ibuprofen acid equivalents per aluminum atom.

9. A composition according to claims 1 or 2 wherein the aluminum ibuprofen salt is one having a ratio of about 2 ibuprofen equivalents per atom of aluminum in the salt.

10. A composition according to claim 2 which consists essentially of, for each 100 ml of suspension,
   (a) about 4.4 to about 14 gms of aluminum ibuprofen salt, which will provide about 4 to about 12 gms of ibuprofen equivalent in a suspension composition;
   (b) about 0.2 to about 1.1 gms of a suspending agent mixture consisting of about 0.18 to about 1.0 gm of microcrystalline cellulose and about 0.02 to about 0.12 gm of sodium carboxymethylcellulose;
   (c) about 0.3 to about 0.7 gm of a polyoxyethylenesorbitan mono$C_{16}$ to $C_{20}$-alkanoic surfactant containing an average of about 18 to about 22 ethyleneoxy groups per surfactant molecule;
   (d) from about 10 to about 25 gms of granular U.S.P. sucrose;
   (e) from about 0.1 to about 0.3 gm of sorbic acid NF;
   (f) from about 0.032 to about 0.05 ml of artificial cherry-vanilla flavor,
   (g) 10% v/v hydrochloric acid aqueous solution, q.s. (for pH adjustment);
   (h) 10% w/v sodium hydroxide aqueous solution, q.s. (for pH adjustment);
   (i) purified water q.s. to make 100 ml of the liquid suspension.

11. A composition according to claims 1 or 2 wherein the aluminum ibuprofen salt is one having a surface area of at least 7.0 square meters per gram.

12. A composition according to claim 2 which includes as component (e) from about 6.25 grams to about 37.5 grams of glucose.

13. A composition according to claim 2 which includes as component (e) from about 2.94 grams to about 17.65 grams of fructose.

14. A composition according to claim 2 which includes as component (e) from about 5 milligrams to about 60 milligrams of sodium saccharin.

15. A composition according to claim 2 which further includes as component (e) from about 166 milligrams to about 1 gram of sodium cyclamate.

* * * * *

UNITED STATES PATENT OFFICE
CERTIFICATE OF CORRECTION

Patent No. 4,361,580  Dated November 30, 1982

Inventor(s) Susanne M. Peck, et al.

It is certified that error appears in the above-identified patent and that said Letters Patent are hereby corrected as shown below:

Title page, first column, [73], should read, "Assignee: The Upjohn Manufacturing Company M" instead of as now shown.

Signed and Sealed this

Twenty-ninth Day of March 1983

[SEAL]

Attest:

GERALD J. MOSSINGHOFF

Attesting Officer  Commissioner of Patents and Trademarks